United States Patent [19]

Strong

[11] 3,968,168
[45] July 6, 1976

[54] P-TERT-BUTYL-DIPHENYLALKANE INSECTICIDES

[75] Inventor: Jerry G. Strong, Warren, N.J.

[73] Assignee: Mobil Oil Corporation, New York, N.Y.

[22] Filed: Aug. 23, 1974

[21] Appl. No.: 499,875

[52] U.S. Cl. .............................. 260/612 R; 424/340
[51] Int. Cl.$^2$ ..................... C07C 43/20; A01N 9/24
[58] Field of Search .................. 260/612 R; 424/340

[56] References Cited
UNITED STATES PATENTS

| | | | |
|---|---|---|---|
| 2,442,760 | 6/1948 | Dieter et al. | 424/340 |
| 3,642,910 | 2/1972 | Holan | 260/612 R |

FOREIGN PATENTS OR APPLICATIONS

| | | | |
|---|---|---|---|
| 688,156 | 6/1964 | Canada | 424/340 |

OTHER PUBLICATIONS

M. Fahmy, et al., J. Agr. Food Chem., 21, 585–590 (1973).
Haller, Wartime Development of Insecticides, Ind. Eng. Chem., 39, 467–473 (1947).
Kirk–Othmer, Encyclopedia of Chem. Term. vol. 11, pp. 691–694 (1966).

Primary Examiner—James O. Thomas, Jr.
Assistant Examiner—G. Breitenstein
Attorney, Agent, or Firm—Charles A. Huggett; Mitchell G. Condos; Howard M. Flournoy

[57] ABSTRACT 1,1-Diphenylalkanes having a p-tert-butyl and a p'-alkoxy group substituted thereon are a novel class of compounds having a broad range of insecticidal activity.

13 Claims, No Drawings

P-TERT-BUTYL-DIPHENYLALKANE INSECTICIDES

CROSS-REFERENCE TO RELATED APPLICATIONS

U.S. application Ser. No. 499,866 filed on the same date herewith and entitled P-Tert-Butyl-Diphenylalkane Insecticides relates to such compounds having p'-alkyl ($C_1$–$C_3$) substitution as opposed to the p'-alkoxy substitution of this application.

BACKGROUND OF THE INVENTION

This invention is directed to a new class of compounds, 1,1-diphenylalkanes bearing p-tert-butyl and a p'-alkoxy ($C_1$–$C_4$) groups, useful as insecticides. This invention is further directed to compositions comprising same and an inert solid or liquid carrier, and a method of using said compounds and compositions in controlling insects.

DESCRIPTION OF THE PRIOR ART

Metcalf, et al. in U.S. Pat. No. 3,787,505 (Reference 1) reported compounds having the following structure wherein R and R' are different and R is selected from the group consisting of $CH_3$, $OCH_3$, $OC_2H_5$ and $OC_3H_7$, and R' is selected from $SCH_3$ and $CH_3$:

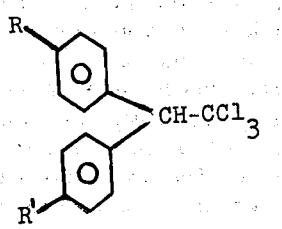

Additionally, the following compounds were reported by M. Fahmy, T. Fukuto, R. Metcalf, and R. Holmstead, *J. Agr. Food Chem.*, 21 585 (1973) (Reference 2).

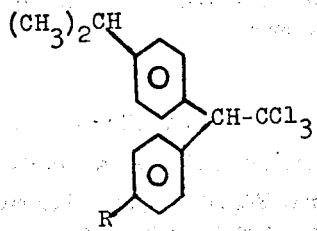

and

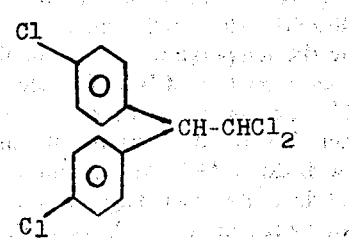

where R is $OCH_3$ and Cl.

Most of these compounds were also described by R. L. Metcalf and T. R. Fukuto, Bull. Wld. Hlth. Org., 38 633, (1968) (Reference 3); Compounds therein not described above include:

wherein R and R' are the same and are selected from Cl, $CH_3$, $C_2H_5$, $CH(CH_3)_2$, $C(CH_3)_3$, $OCH_3$ and $OC_2H_5$. The compound wherein R and R' are Cl is the well known insecticide DDT. The compound wherein R and R' are Cl, and wherein $CCl_3$ is replaced by $CHCl_2$ is the insecticide DDD.

Structure-activity relationships and theories derived from such prior art strongly suggest that compounds according to the present invention should be insecticidally inactive. For example, it is stated in reference 3, page 637 with regard to alterations of the ring substituents of DDT, "substitution of a single p-$CH_3$ for p-Cl produced a substance considerably more effective-(insecticidally) than the isosteric DDT. However, compounds with larger alkyl groups in the p,p' positions- isopropyl, butyl, pentyl and dodecyl were completely inactive." This is reinforced later in the summary of said reference wherein it is stated that insect activity of DDT analogs is optimal when p,p'-Cl are substituted by small relatively non-polar groups such as F, Cl, Br, $CH_3$, $OCH_3$, $C_2H_5$ and $OC_2H_5$.

A more detailed analysis of structure-activity relationships in DDT analogs presented in Reference 2 concludes that for maximum activity the overall size of the molecule is critical and deviation from the size of the DDT molecule result in reduced activity.

Accordingly, one would conclude from this that any DDT analogs bearing the large p-tert-butyl group such as the compounds of the present invention, all of which are thus much larger than DDT, would be insecticidally inactive.

The insecticide screening data presented below clearly shows that this is not the case. Thus, the activity of the new compounds is surprising and could not have been predicted by currently held theories of insecticidal structure and activity relationships.

SUMMARY OF THE INVENTION

This invention provides new 1,1-diphenylalkanes wherein the phenyl groups are substituted at the para position one by tert-butyl and the other by alkoxy substituents. These new compounds are highly effective in combating various insect classes including lepidoptera, e.g. southern armyworm, and coleoptera, e.g., Mexican bean beetle. These two classes of insects represent the largest group of insect pests in terms of the annual damage they inflict on crops.

The compounds embodied in this invention have the following general structure:

wherein R is alkoxy ($C_1$ to $C_4$) i.e. selected from the group consisting of $OCH_3$, $OC_2H_5$, $OC_3H_7$ and $OC_4H_9$, and $a$, $b$ and $c$ are selected from the group consisting of chloro, alkyl ($c_1$–$C_2$) and hydrogen. The compounds of the present invention, unlike DDT and DDD, are expected to be biodegradable and non-persistent in the environment. R. L. Metcalf, et al. report in the Bull. Wld. Hlth. Org., 44 363 (1971) that DDT analogs having substituent groups (e.g. alkoxy and alkyl) readily attacked by multifunction oxidase enzymes present in the environment undergo substantial biological degradation and do not appear to be readily stored or concentrated in animal tissues or food chains. Furthermore, as pointed out by I. P. Kapoor, et al., *J. Agr. Food Chem.*, 21 310 (1973), a single biodegradable substituent is sufficient to impart a substantial rate of biodegradability to the compound.

DESCRIPTION OF THE PREFERRED EMBODIMENTS

Non-Limiting Examples 1-(p-tert-Butylphenyl)-1-(p'-ethoxyphenyl)ethane;
1-(p-tert-Butylphenyl)-1-(p'-ethoxyphenyl)propane;
1-(p-tert-Butylphenyl)-1-(p'-ethoxyphenyl)butane;
1-(p-tert-Butylphenyl)-1-(p'-methoxyphenyl)-2-chloroethane;
1-(p-tert-Butylphenyl)-1-(p'-ethoxyphenyl)-2-chloroethane;
1-(p-tert-Butylphenyl)-1-(p'-methoxyphenyl)-2-chloropropane;
1-(p-tert-Butylphenyl)-1-(p'-methoxyphenyl)-2-chlorobutane;
1-(p-tert-Butylphenyl)-1-(p'-propoxyphenyl)-2,2-dichloroethane;
1-(p-tert-Butylphenyl)-1-(p'-ethoxyphenyl)-2,2-dichloropropane;
1-(p-tert-Butylphenyl)-1-(p'-ethoxyphenyl)-2,3-dichloropropane;
1-(p-tert-Butylphenyl)-1-(p'-propoxyphenyl)-2,2,2-trichloroethane;
1-(p-tert-Butylphenyl)-1-(p'-methoxyphenyl)-2,2,2-trichloroethane;
1-(p-tert-Butylphenyl)-1-(p'-methoxyphenyl)-2-methylpropane;
1-(p-tert-Butylphenyl)-1-(p'-ethoxyphenyl)-2,2-dimethylpropane;
1-(p-tert-Butylphenyl)-1-(p'-methoxyphenyl)-2,2-dimethylpropane, etc.

In general, the compounds of this invention are prepared by condensing tert-butylbenzene with an appropriately substituted carboxylic acid chloride and/or chloral in the presence of a suitable catalyst, e.g., aluminum chloride.

The resulting ketones are reduced to the corresponding alcohols using the convenient RED-AL™ reducing reagent available from Aldrich Chemical Company.

The purified alcohols are then condensed with an appropriate alkoxybenzene in the presence of sulfuric acid. A solvent such as dichloromethane, ethylene chloride or acetic acid may be employed or excess alkoxybenzene may serve as solvent.

The starting materials—tert-butylbenzene, carboxylic acid chlorides, and alkoxybenzenes are articles of commerce.

EXAMPLE 1

1-p-tert-Butylphenyl-2,2,2-trichloroethanol

A solution of 22 g (0.15 mole) of chloral and 15g of tert-butylbenzene was added in ten portions alternatively with 4.4g (0.03 mole) of aluminum chloride to a 120g portion of tert-butylbenzene with vigorous stirring at 5°C. The mixture was stirred at 20°C. for 0.5 hr. and again cooled to 5°C. before 40 ml of 6N HCl was added dropwise. The mixture was diluted with 20 ml of water and the organic products were extracted into ethyl ether (2 × 100 ml). The etheral solution was washed with 5% HCl, water, aqueous sodium carbonate and brine, dried over magnesium sulfate and concentrated. A 27g portion of the 33g residue was distilled via short path to provide 18.4g of a colorless, viscous product: Bp 144°C (0.2mm); ir (film) 2.85 (s), 3.4 (s), 9.4 (s), 12.1 (s), 12.8 (s) microns; nmr ($CDCl_3$) 7.40 (4H, m), 5.06 (1H,s), 3.56 (1H, s), 1.28 (9H, s) ppm.

EXAMPLE 2

1-p-tert-Butylphenyl-1-p-ethoxyphenyl-2,2,2-trichloroethane

A mixture of 15g (0.12 mole) of phenetole and 20 ml of 96% sulfuric acid was prepared at 0°–5°C and to this was added over 15 min. at 0°–5°C a solution of 5.6g (0.02 mole) of Example 1 in 10 ml of dichloromethane. The mixture was vigorously stirred for 2 hrs. while the temperature rose to ambient and then poured onto 100 ml of crushed ice. The organic products were extracted into ethyl ether and the etheral solution was washed with water, aqueous bicarbonate and with brine, dried over magnesium sulfate and concentrated on the steam bath at 1.0 mm. Obtained was 6g of a viscous liquid. A VPC analysis indicated a mixture of 85% p,p'-isomer and 15% o,p'-isomer. Ir (film) 3.4(s), 6.6 (s), 8.0 (s), 8.5 (s), 11.9 (s), 12.9 (s) microns; nmr ($CDCl_3$) 7.6 to 6.7 (8H, m), 4.94 (1H, s), 3.92 (2H, q), 1.26 (3H t), 1.25 (9H, s) ppm.

EXAMPLE 3

4'-tert-Butyl-2,2-dichloroacetophenone

A solution of 74g (0.5 mole) of dichloroacetyl chloride and 67g (0.5 mole) of tert-butylbenzene was added over 0.5 hr. at 0°–5°C to a vigorously stirred mixture of 68g (0.5 mole) of aluminum chloride and 75 ml of carbon disulfide. The reaction mixture was stirred for 4 hrs. while the temperature rose to ambient and then poured onto a mixture of 500 ml of ice and 100 ml of 12M HCl. The organic products were extracted into ethyl ether (2 × 400 ml) and the etheral solution was washed with dilute HCl, water, aqueous bicarbonate and with brine, dried over magnesium sulfate and concentrated. Obtained was 120g of dark liquid which crystalized from cold (−40°C) 30–60 pet. ether to provide 70g of a white solid after several washings with cold pet. ether: mp 47°–49°C; ir (KBr) 3.4 (m), 5.9 (s), 6.3 (s), 11.7 (s), 12.6 (s); nmr ($CDCl_3$) 6.7 (1H, s) ppm.

EXAMPLE 4

1-p-tert-Butylphenyl-2,2-dichloroethanol

A 50 ml portion (0.2 mole) of a 70% RED-AL solution (Aldrich Chemical Company) was added over 0.5 hr. to a solution of 49g (0.2 mole) of Example 3 in 300 ml of benzene. Dry nitrogen blanketed the reaction surface and the temperature was controlled at 20°–30°C. After stirring for 2 hrs. at ambient, the solution was cooled to 10°C and the excess reducing agent was neutralized by the dropwise addition of 30 ml of 20% sulfuric acid. The white solid which separated was filtered and washed with benzene and the benzene filtrates were concentrated to afford 50g of a clear liquid. A 38g portion was distilled via short path to provide 35g of a clear, colorless liquid: Bp 112°–118°C (0.5 mm); ir (film) 2.9 (s), 3.4 (s), 11.8 (s), 12.7 (s) microns; nmr (CDCl$_3$) 7.23 (4H, m), 5.65 (1H, d), 4.78 (1H, d), 3.40 (1H, s), 1.25 (9H, s) ppm.

EXAMPLE 5

1-p-tert-Butylphenyl-1-p-methoxyphenyl-2,2-dichloroethane

The procedure of Example 2 was followed for the reaction of 7.4g (0.03 mole) of Example 4 with 20g (0.18 mole) of anisole in 20 ml of sulfuric acid and 10 ml of carbon tetrachloride. Obtained was 9.6g of a semi-solid which crystallized from hexane to provide 7.5g of a white powder: mp 108°–110°C; ir (KBr) 3.4 (m), 6.2 (m), 6.7 (s), 8.0 (s), 9.7 (m), 13.3 (s) microns; nmr (CDCl$_3$) 7.23 (4H, s), 6.98 (4H, d of d), 6.28 (1H, d), 4.46 (1H, d), 3.63 (3H, s), 1.21 (9H, s) ppm. A VPC analysis indicated a mixture of 85% p,p'-isomer, 15% o,p'-isomer.

EXAMPLE 6

1-p-tert-Butylphenyl-1-p-ethoxyphenyl-2,2-dichloroethane

The procedure of Example 2 was followed for the reaction of 7.4g (0.03 mole) of Example 4 with 22g (0.18 mole) of phenetole in 20 ml of sulfuric acid and 10 ml of carbon tetrachloride. Obtained was 9.0g of a viscous liquid which crystallized from hexane-pet ether to afford 6.8g of a white solid: mp 97°–99°C: ir (KBr) 3.4 (m), 6.7 (m), 8.0 (s), 9.6 (m), 13.3 (m) microns; nmr (CDCl$_3$) 7.23 (4H, s), 7.00 (4H, d of d), 6.30 (1H, d), 4.47 (1H, d), 3.94 (2H, q), 1.22 (9H, s) ppm. A VPC analysis indicated 85% p,p'-isomer, 15% o,p'-isomer.

EXAMPLE 7

4'tert-Butylbutyrophenone

The procedure of Example 3 was followed for the reaction of 53g (0.5 mole) of butyryl chloride with 67g (0.5 mole) of tert-butyl benzene. Obtained after high vacuum concentration was 94g of a clear liquid. A VPC analysis indicated a pure product. Ir (film) 3.5 (s), 5.9 (s) microns; nmr (CDCl$_3$) 7.65 (4H, center doublet of doublets), 2.9 (2H, t), 1.75 (2H, sextet), 1.3 (9H, s), 0.95 (3H, t) ppm.

EXAMPLE 8

4'-tert-Butyl-2-chlorobutyrophenone

To a solution of 51g (0.25 mole) of Example 7 in 200 ml of carbontetrachloride was added portionwise 38g (0.28 mole) of sulfuryl chloride and the reaction solution was heated to 70°C for 1.5 hr. The solution was then washed with water, aqueous bicarbonate and brine, dried over magnesium sulfate and concentrated. Obtained was 56g of a liquid which was distilled to afford 33g of a center fraction of clear, colorless product; Bp 113°–118° (0.4 mm); ir (film) 3.4 (m), 5.9 (s), 6.3 (m), 7.8 (m), 11.7 (m) microns; nmr (CDCl$_3$) 7.67 (4H, d of d), 5.03 (1H, t) 2.04 (2H, quintet), 1.28 (9H, s), 1.11 (3H, t) ppm.

EXAMPLE 9

1-(p-tert-Butylphenyl)-2-chlorobutanol

The procedure of Example 4 was followed for the reaction of 35.7g (0.15 mole) of Example 8 with 37.5 ml (0.15 mole) of RED-AL. Obtained was 32.5g of a liquid product which was distilled to afford 26.7g of a colorless liquid; Bp 112°–118°C (0.5 mm); ir (film) 2.9 (m), 3.4 (s), 6.9 (m), 11.9 (m) microns; nmr (CDCl$_3$) 7.28 (4H, d of d), 4.70 (1H, d of d), 4.02 (1H, m), 2.70 (1H, broad), 1.65 (2H, m), 1.25 (9H, s), 0.95 (3H, t) ppm.

EXAMPLE 10

1-p-tert-Butylphenyl-1-p-ethoxyphenyl-2-chlorobutane

The procedure of Example 2 was followed for the reaction of 6.0g (0.025 mole) of Example 9 with 22g (0.18 mole) of phenetole. Obtained was 7.6g of a clear, colorless liquid product: ir (film) 3.5 (s), 6.7 (m), 8.1 (s), 9.6 (m), 12.2 (m) microns; nmr (CDCl$_3$) 7.53–6.68 (8H,m), 4.51 (1H, m), 4.03 (1H, d), 3.90 (2H, q), 1.62 (2H, m), 1.30 (3H, t), 1.20 (9H, s), 1.00 (3H, t) ppm. A VPC analysis indicated 75% p,p'-isomer, 15% o,p'-isomer, 10% other products.

EXAMPLE 11

4'-tert-Butyl-2-methylpropiophenone

The procedure of Example 3 was followed for the reaction of 67g (0.5 mole) of tert-butylbenzene with 53.3g (0.5 mole) of isobutyryl chloride. Obtained after high vacuum concentration was 88g of a clear liquid; ir (film) 3.4 (m), 5.95 (s), 8.2 (s), 10.2 (s) microns; nmr (CDCl$_3$) 7.65 (4H, d of d) 3.50 (1H, quintet), 1.28 (9H, s) 1.15(6H, d) ppm. A VPC analysis indicated one pure product.

EXAMPLE 12

1-p-tert-Butylphenyl-2-methylpropanol

The procedure of Example 4 was followed for the reaction of 40.8g (0.2 mole) of Example 11 with 50 ml (0.2 mole) of RED-AL. Obtained was 38.7 g of a clear liquid which was distilled to afford 35.4g of a clear colorless liquid: Bp 90°–94° (0.3 mm); ir (film) 2.95 (m), 3.5 (s), 6.9 (m), 7.3 (m), 9.9 (m) microns; nmr (CDCl$_3$) 7.15 (4H, q), 4.14 (1H, d), 2.59 (1H, s), 1.82 (1H, sextet), 1.23 (9H, s), 0.88 (3H, d), 0.65 (3H, d) ppm.

EXAMPLE 13

1-p-tert-Butylphenyl-1-p-ethoxyphenyl-2-methylpropane

The procedure of Example 2 was followed for the reaction of 6.2g (0.03 mole) of Example 12 with 22g (0.18 mole) of phenetole. Obtained was 7.6g of a clear liquid which crystallized from 30°–60 pet ether at −60°C to provide 3.8g of a white solid: mp 68°–71°C; ir (KBr) 3.4 (m), 6.6 (m), 8.1 (s), 9.5 (m), 12.2 (m)

microns; nmr (CDCl$_3$) 7.17 (4H, s), 6.92 (4H d of d), 3.91 (2H, q), 3.30 (1H, d), 2.40 (1H, m) 1.38 (3H, d), 1.20 (9H, s), 0.86 (3H, d) ppm. A VPC analysis indicated a mixture of 90% p,p'-isomer, 10% o,p'-isomer.

EXAMPLE 14

4'-tert-Butyl-2-methylbutyrophenone

The procedure of Example 3 was followed for the reaction of 60g (0.5 mole) of 2-methylbutyryl chloride with 67g (0.5 mole) of tert-butylbenzene. Obtained was 98.6g of a clear liquid: ir (film) 3.4 (s), 5.95 (s), 8.2 (m) microns; nmr (CDCl$_3$) 7.66 (4H, d of d) 3.37 (1H, q), 1.77 (2H, m), 1.28 (9H, s), 1.16 (3H, d), 0.88 (3H, t) ppm. A VPC analysis indicated a single pure product.

EXAMPLE 15

1-p-tert-Butylphenyl-2-methylbutanol

The procedure of Example 4 was followed for the reaction of 43.6g (0.2 mole) of Example 14 with 50 ml (0.2 mole) of RED-AL. Obtained was 45.2g of a clear liquid which was distilled to provide 38.4g of a clear, colorless liquid product: Bp 93°–94°C (0.2 mm) ir (film) 2.9 (s), 3.4 (s), 6.8 (m), 12.1 (m) microns; nmr (CDCl$_3$) 7.20 (4H, d of d), 4.31 (1H d of d), 2.19 (1H, s), 1.65 (1H, m), 1.24 (9H, s), 1.60–0.60 (8H, m) ppm. A VPC analysis indicated a single pure product.

EXAMPLE 16

1-p-tert-Butylphenyl-1-p-ethoxyphenyl-2-methylbutane

The procedure of Example 2 was followed for the reaction of 6.6g (0.03 mole) of Example 15 with 22g (0.18 mole) of phenetole. Obtained following a high vacuum concentration was 6.3g of a clear colorless liquid: ir (film) 3.4 (s), 6.7 (m), 8.1 (s), 9.6 (m) microns; nmr (CDCl$_3$) 7.13 (4H, s), 6.92 (4H d of d), 3.85 (2H, q), 3.4 (1H, d), 2.2 (1H, m), 1.20 (9H, s), 1.7–0.7 (11H, m) ppm. A VPC analysis indicated a composition of 95% p,p'-isomer, 5% o,p'-isomer.

EXAMPLE 17

4'-tert-Butyl-2-chloropropiophenone

The procedure of Example 3 was followed for the reaction of 63.5g (0.5 mole) of 2-chloropropionyl chloride with 67g (0.5 mole) of tert-butylbenzene. Obtained after high vacuum concentration was 100g of clear, yellow liquid product: ir (film) 3.4 (s), 5.9 (s), 6.3 (s), 8.0 (s), 10.5 (s), 11.8 (s) microns; nmr (CDCl$_3$) 7.67 (4H, d of d), 5.21 (1H, q), 1.67 (3H, d), 1.28 (9H, s) ppm. A VPC analysis indicated one pure product.

EXAMPLE 18

1-p-tert-Butylphenyl-2-chloropropanol

The procedure of Example 4 was followed for the reaction of 67.4g (0.3 mole) of Example 17 with 75 ml of RED-AL in 400 ml of benzene. Obtained following vacuum concentration was 69g of a clear liquid which was distilled to afford 53g of clear, colorless liquid product: Bp 100°–102° (0.2 mm); ir (film) 2.9 (s), 3.4 (s), 6.9 (m), 7.3 (m), 9.1 (m), 9.7 (m), 10.0 (m), 11.9 (m) microns. A VPC analysis indicated one pure product.

EXAMPLE 19

1-p-tert-Butylphenyl-1-p-ethoxyphenyl-2-chloropropane

The procedure of Example 2 was followed for the reaction of 6.8g (0.03 mole) of Example 18 with 22g (0.18 mole) of phenetole in 10 ml of dichloromethane and 20 ml of sulfuric acid. Obtained following recrystallization of the work-up residue from 20-40 pet ether was 5.2g of a white solid product; mp 74°–75°C; ir (CCl$_4$) 3.4 (s), 8.0 (s), 8.5 (m), 9.5 (m), 15.2 (s), 15.4 (m) microns; nmr (CDCl$_3$) 7.4 to 6.7 (8H, m), 4.68 (1H, m), 3.8–4.1 (3H, m), 1.44 (3H, d), 1.33 (3H, t), 1.22 (9H, s) ppm. A VPC analysis indicated a product purity of 100 percent.

EXAMPLE 20

The novel p-tert-butyl-1,1-diphenylalkanes of this invention were evaluated in standard greenhouse insecticide tests using housefly (HF, bait test), Mexican bean beetle (MB), southern armyworm (SA) and yellow fever mosquito larvae (YF). The rates of application were 500, 100, 10 and 1 ppm of active ingredient (p,p'-isomer).

The known compounds methyl methoxychlor, methyl ethoxychlor, methoxychlor and DDT were included for comparisons in these tests. According to references 1, 2 and 3, these are the most broadly effective of the known insecticidal DDT analogs. The results as set forth below indicate the percent control of each insect species.

| COMPOUND | RATE (PPM) | HF | MB | SA | YF |
|---|---|---|---|---|---|
| Example 2 | 500 | 100 | 100 | 80 | — |
|  | 100 | 30 | 30 | 10 | — |
|  | 10 | — | — | — | 100 |
|  | 1 | — | — | — | 60 |
| Example 5 | 500 | 100 | 90 | 10 | — |
|  | 100 | 10 | 20 | — | — |
|  | 10 | — | — | — | 80 |
|  | 1 | — | — | — | 60 |
| Example 6 | 500 | 100 | 100 | 80 | — |
|  | 100 | 100 | 90 | 20 | — |
|  | 10 | — | — | — | 100 |
|  | 1 | — | — | — | 80 |
| Example 10 | 500 | 90 | 100 | 100 | — |
|  | 100 | 40 | 30 | 70 | — |
|  | 10 | — | — | — | 80 |
|  | 1 | — | — | — | 60 |
| Example 13 | 500 | 60 | 90 | 100 | — |
|  | 100 | 10 | 10 | 20 | — |
|  | 10 | — | — | — | 100 |
|  | 1 | — | — | — | 80 |
| Example 16 | 500 | 40 | 60 | 70 | — |
|  | 100 | 10 | 10 | 10 | — |
|  | 10 | — | — | — | 60 |
|  | 1 | — | — | — | 20 |
| Example 19 | 500 | 90 | 100 | 100 | — |
|  | 100 | 50 | 100 | 10 | — |
|  | 10 | — | — | — | 100 |
|  | 1 | — | — | — | 80 |
| Methyl Methoxychlor | 500 | 100 | 100 | 10 | — |
|  | 100 | 90 | 80 | — | — |
|  | 10 | — | — | — | 100 |
|  | 1 | — | — | — | 100 |
| Methyl Ethoxychlor | 500 | 90 | 100 | 20 | — |
|  | 100 | 20 | 100 | — | — |
|  | 10 | — | 30 | — | 100 |
|  | 1 | — | — | — | 100 |
| Methoxychlor | 500 | 100 | 100 | 10 | — |
|  | 100 | 90 | 100 | — | — |
|  | 10 | — | — | — | 100 |
|  | 1 | — | — | — | 100 |
| DDT | 500 | 100 | 40 | 100 | — |
|  | 100 | 100 | 10 | 60 | — |
|  | 10 | — | — | — | 100 |
|  | 1 | — | — | — | 100 |

TEST METHODS

House Fly; 1 milliliter of an aqueous solution or suspension of the test compound was pipeted into a 9 cm. petri dish containing filter paper and 0.1 gram of granular sugar. Ten adult house flies were admitted and the dish closed. Observations were made periodically for knockdown and at 24 hours for mortality.

Southern army worm and Mexican Bean Bettle; lima bean leaves of uniform size were momentarily dipped in a water-acetone solution of the test compound and the treated leaves were then placed on moistened filter paper in 9 cm petri dishes and allowed to air dry. When dry, five, third, or fourth instar larvae were introduced and encouraged to feed on the treated foliage by means of confinement. The dishes were closed and held for observation of mortality and feeding during a 48 to 72 hour period.

Early fourth stage mosquito larvae are exposed to solutions, emulsions or suspensions of the materials in water. The compounds are dissolved in acetone and added to the water; water-soluble compounds remain in solution and the others become finely divided suspensions. Compounds are screened initially at 10 ppm using approximately 5 larvae per 100 ml of treated water. Each treatment is replicated twice.

From the data presented in Example 20, it is noted that contrary to currently held theories of structure-activity relationships in DDT analogs, the compounds of the present invention are effective insecticides on a broad range of insect species.

It is also noted that the compounds of the present invention are markedly effective for the control of the difficult to control southern armyworm which is an obvious deficiency of most of even the more active of the previously reported DDT analogs.

Although the present invention has been described with the preferred embodiments, it is to be understood that modifications and variations may be resorted to without departing from the spirit and scope of the invention, as those skilled in the art will readily understand.

I claim:

1. A compound having the following general structure:

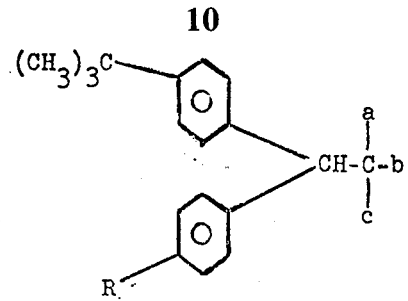

wherein R is selected from the group consisting of $OCH_3$, $OC_2H_5$, $OC_3H_7$ and $OC_4H_9$ and a, b and c are the same or different and are each selected from the group consisting of chloro, alkyl ($C_1$–$C_3$) and hydrogen.

2. The compound of claim 1 wherein R is selected from the group consisting of $OCH_3$ and $OC_2H_5$ and $a$, $b$ and $c$ are each selected from the group consisting of chloro, alkyl ($C_1$–$C_2$) and hydrogen.

3. The compound of claim 1 wherein R is $OC_2H_5$ and $a$, $b$ and $c$ are each chloro.

4. The compound of claim 1 wherein R is $OCH_3$, $a$ and $c$ are chloro and $b$ is hydrogen.

5. The compound of claim 1 wherein R is $OC_2H_5$, $a$ and $c$ are chloro and $b$ is hydrogen.

6. The compound of claim 1 wherein R is $OC_2H_5$, $a$ is chloro, $b$ is ethyl and $c$ is hydrogen.

7. The compound of claim 1 wherein R is $OC_2H_5$, $a$ and $b$ are methyl and $c$ is hydrogen.

8. The compound of claim 1 wherein R is $OC_2H_5$, $a$ is methyl, $b$ is ethyl and $c$ is hydrogen.

9. The compound of claim 1 wherein R is $OC_2H_5$, $a$ is chloro, $b$ is methyl and $c$ is hydrogen.

10. A composition comprising an insecticidally effective amount of a compound, as defined in claim 1, and an inert solid or liquid carrier therefor.

11. A composition comprising an insecticidally effective amount of a compound, as defined in claim 2, and an inert solid or liquid carrier therefor.

12. A method of using a composition as defined in claim 10, comprising applying to an insect or to its environment an insecticidally effective amount of said composition.

13. A method of using the composition as defined in claim 11 comprising applying to an insect or to its environment an insecticidally effective amount of said composition.

* * * * *